United States Patent [19]

Meador et al.

[11] Patent Number: 5,892,096
[45] Date of Patent: Apr. 6, 1999

[54] NON-SUBLIMING MID-UV DYES AND ULTRA-THIN ORGANIC ARCS HAVING DIFFERENTIAL SOLUBILITY

[75] Inventors: Jim D. Meador, Ballwin; Xie Shao, Rolla; Vandana Krishnamurthy, Rolla; Earnest C. Murphy, Rolla; Tony D. Flaim, St. James; Terry Lowell Brewer, Rolla, all of Mo.

[73] Assignee: Brewer Science, Inc., Rolla, Mo.

[21] Appl. No.: 598,711

[22] Filed: Feb. 8, 1996

Related U.S. Application Data

[62] Division of Ser. No. 336,340, Nov. 9, 1994.
[51] Int. Cl.$^6$ .................................................. C07C 255/09
[52] U.S. Cl. ............................................ 558/393; 558/402
[58] Field of Search .............................................. 558/402

[56] References Cited

U.S. PATENT DOCUMENTS

| 4,719,166 | 1/1988 | Blevins et al. | 430/166 |
| 5,139,918 | 8/1992 | Goel | 430/166 |
| 5,215,876 | 6/1993 | Pruett et al. | |

*Primary Examiner*—Johann Richter
*Assistant Examiner*—Taofiq Solola
*Attorney, Agent, or Firm*—Veo Peoples, Jr.; J. William Stader; Peoples & Hale

[57] ABSTRACT

Mid-UV dyes enabling ultra thin antireflection coatings for multi-layer i-line photoetching are produced from bichalcones; bis-a-cyanoacrylates/bis-cyanoacrylamides; and 1.4 divinylbenzenes. The dyes are nonsubliminal and differentially insoluble in standard photoresist solvents.

2 Claims, 2 Drawing Sheets

FIG. 2

NON-SUBLIMING MID-UV DYES AND ULTRA-THIN ORGANIC ARCS HAVING DIFFERENTIAL SOLUBILITY

This application is a division of application Ser. No. 08/336,340, filed Nov. 9, 1994.

BACKGROUND OF THE INVENTION

1. Field of the Invention

This invention generally relates to Anti-Reflective Coatings (ARCs) for multi-layer i-line photoresist systems. More particularly, it relates to improved i-line dyes, which dyes have differential solubility characteristics for use in ultra-thin layer ARCs.

2. Background of the Prior Art

Recently, integrated circuit (IC) manufacturers when printing submicron feature sizes in the range of 0.35–0.70 microns have relied upon mid-ultraviolet (mid-UV) sensitive photoresist. The principal exposure wavelength for these photoresists is 365 nm, which corresponds to the i-line spectral peak of the Hg—Xe arc lamp. The use of this shorter wavelength, as compared to the 436 nm g-line peak, permits greater resolution and broadens depth of focus. Thus, the term "i-line resist" has been used inter-changeably with "mid-uv photoresist". The resolution of i-line resists can be further enhanced by providing substrate reflection control. This can be achieved in two ways. The first way is by adding dye into the resist at some expense to photospeed and feature profile quality. The second way is by employing a multi-layer resist scheme wherein a dyed bottom layer plays the light absorbing role.

Two types of multi-layer schemes have been used in the industry. At one time, relatively thick (ca. 1 micron) bottom layers having low dye concentration were popular. It is desirable that those bottom layers now be replaced by high optical density, ultra-thin ARCs to simplify the etching of the ARC, which would lead to improved critical dimension control. However, the development of ultra-thin ARCs for i-line applications has been hampered by the unavailability of suitable dyes.

Some advances have been made in developing prior art i-line dyes for single-layer-resist-type processes. However, there is a drawback to such dyes, as well as dyes designed for the multi-layer resist processes, which accommodate a relatively thick (1.3 micron) bottom or sublayer ARC. This drawback of the prior art and their attendant i-line dyes are explained below.

An example of a classically cited strongly absorbant mid-UV i-line dye in the prior art is Michler's ketone (bis-N,N-dimethylaminobenzophenone). In order to employ Michler's Ketone in photo-etch processing, conditions peculiar to such processing must be accommodated. That is, it is common to process photoresist layers and their ARCs at temperatures as high as 200° C. Unfortunately, Michler's Ketone, like many other prospective i-line dyes, tends to sublime or volatize at such temperatures, and therefore lacks the requisite thermal stability to undergo such processing.

In U.S. Pat. No. 4,719,166, R. W. Blevins disclosed a single layer non-subliming resist system which used butadienyls as i-line dyes. The dyes surprisingly overcame the tendency of previously known mid-UV dyes to sublime at processing temperatures near 200° C., even though the molecular weight of the butadienyls was less than the molecular weight which would have predicted thermal stability. The predictably higher molecular weight dyes, as taught by Blevins, were to be avoided because they would not exhibit good solubility in photoresist solvents such as chlorobenzene and ethoxyethyl acetate. A drawback of these dyes is that the process used to produce the butadienyls yields the butadienyls at an unacceptably low 10%. More importantly, these dyes are so soluble that they cannot be used in ultra-thin ARCs without leaching into the photoresist top layer of multi-layer systems.

In U.S. Pat. No. 5,139,918, Mr. A. Goel disclosed a multi-layer resist system which employed butadiene or bromine substituted butadienes as the i-line dye, especially N,N'-dibutyl-N,N'-di(1-(4,4-dicyano-1,3-butadiene))-1,6-hexanediamine. Although this dye system is acceptable for the relatively thick (1.3 micron) bottom layers of the multi-layer resist systems, it is ineffective for ultra-thin ARCs. Like the single layer i-line dyes, these butadienes are highly soluble in photoresist solvent systems. Therefore, although the 1.3 micron thickness of the bottom layer ARC serves to lessen the leaching, ultra-thin ARCs suffer so much loss of dye that substrate reflection cannot be controlled.

The drawback to each of these prior art i-line dyes is that they lack effective differential solubility. That is, the very same solubility in photoresist solvents such as chlorobenzene and ethyoxyethyl acetate which allow the dyes to be formulated in known polymer coating systems such as polymethyl methacrylate (PMMA), will either limit dye use to single layer photoresist systems, or risk, in multi-layer systems, having the dye leaching out of the ARC layer into the top photoresist layer.

Accordingly, a non-subliming i-line dye having strong mid-UV absorptivity which would be sufficiently soluble in ultra-thin ARC layers to produce an effective high optical density in layers having less that 0.25 microns thicknesses, yet characterized by being insoluble in photoresist solvents, would represent an unexpected advancement in the art and fulfill a long felt need in the industry.

SUMMARY OF THE INVENTION

It is an object of the present invention to provide an i-line dye system with sufficiently selective differential solubility to avoid leaching out of ultra-thin ARCs.

It is a further object of the present invention to provide a non-subliming i-line dye at 200° C. which would be soluble in ARC solvent but not photoresist solvent.

It is a still further object to provide a non-subliming i-line dye which can be produced in commercially acceptable yields.

Applicant has developed mid-UV dyes which enable ultra-thin ARCs for multi-layer i-line photetching where the ARC can be sandwiched between a top layer i-line photoresist and substrate without risk of the dye leaching into the photoresist. The dye is termed differentially insoluble in standard photoresist solvents.

Dyes of the present invention can be generally described as dienyl compounds having molecular weights greater than 300 g/mol and which are soluble in NMP but not chlorobenzene or 2-ethoxy-ethyl acetate. These dyes may be described as fitting in one of the following three chemical families of structures:

1. bischalcones
2. bis-a-cyanoacrylates (and bis-a-cyanoacrylamides)
3. 1,4-divinylbenzenes

The i-line dyes of the present invention can all be prepared in high yield from low cost, commercially available starting materials.

DETAILED DESCRIPTION OF THE PREFERRED EMBODIMENTS

In accordance with the present invention, a first preferred family of i-line dyes having the requisite differential solubility and non-subliming characteristics comprise symmetrical structures having two identical chalcone moieties linked by appropriate spacer groups ($R_2$). The bischalcone compounds may be represented by the following general formula:

where $R_1$ is chosen from the group:

where $R_2$ is selected from the group:
—O—$CH_2$—$CH_2$—O—CO—$R_4$—CO—O—$CH_2$—$CH_2$—O—; —NH—CO—$R_4$—CO—NH—;
—O—$R_5$—O—; —$CH_2$—; —O—; —S—;
where $R_3$=—H, —$CH_3$, halogen, —OH, or —$OCH_3$;
where $R_4$ is chosen from the group:

where $R_5$ is an aliphatic, cycloaliphatic, or alkylaryl divalent radical such as:

—$CH_2$—$CH_2$—    —$CH_2$—$CH_2$—$CH_2$—    —$(CH_2)_6$—

—$CH_2$—$CH(CH_3)$—$CH_2$—$CH_2$—$CH_2$—

—$CH_2$—$CH_2$—O—$CH_2$—$CH_2$—

A particularly preferred representative dye of this family is as follows:

In accordance with the present invention, a second family of preferred i-line dyes having the requisite differential solubility and non-subliming characteristics are bis-a-cyanoacrylates and bis-a-cyanoacrylamides having the general formula:

where $R_1$ is defined as above and where $R_6$ is selected from the group:

and where $R_4$ and $R_5$ are defined as above.

A particularly preferred representative dye of this family is as follows:

Likewise, in accordance with the present invention, a third family of preferred i-line dyes having the requisite differential solubility and non-subliming characteristics are the 1,4-divinylbenzenes having the general formula:

where $R_7$ is selected from the group:

where $R_8$ is an alkyl, cycloalkyl, or alkylaryl monovalent radical such as methyl, ethyl, cyclohexyl, or benzyl; where $R_9$, $R_{10}$ and/or $R_{11}$ are —H, —$CH_3$, —OH, —$OCH_3$, halogen, or —O—$CH_2$—$CH_2$—OH;

and where [A] is a monovalent anion such as chloride, bromide, tosylate or methanesulfonate.

A particularly preferred representative dye of this family is as follows:

The characteristics of the dye compounds of the present invention are:

1. exhibiting low solubility (<2 wt. %) in commonly used photoresist solvents such as ethylene (propylene) glycol monomethyl ether acetate (EGMEA and PGMEA), chlorobenzene, butyl acetate, 3-ethoxyethyl propionate, and ethyl lactate;

2. exhibiting solubility to >1.5 wt. % in preferred solvent systems for ultra-thin bottom anti-reflective coatings, e.g., N-methylpyrrolidone, g-butyrolactone, tetrahydrofurfuryl alcohol, and mixtures thereof with higher volatility cosolvents such as cyclohexanone, diglyme, and diacetone alcohol;

3. possessing a molar extinction coefficient (expressed in L/mol-cm) in excess of 10,000 and, more preferably, in excess of 20,000 at i-line;

4. remaining effectively non-subliming over the temperature range 100°–220° C. when the dye is present in an ultra-thin anti-reflective coating applied onto a semiconductor substrate and when said coating is baked on a hot plate within the stated temperature range for 10–120 seconds.

These compounds unexpectedly enable i-line ARCs having ultra-thin thicknesses of less than 0.25 microns, preferably 0.05 to 0.20 microns. The ARCs comprise a solvent (or solvent mixture), an organic polymer binder and the i-line dye(s). The dyes will be present in an amount of 25 wt. % to 60 wt. % thus providing high film absorbance at i-line ranging typically from 0.3/1000 Å to 0.9/1000 Å. Despite the ultra-thin characteristics and heavy dye loading of the ARC, there is no microscopic intermixing (defined as less than a 0.01 micron zone centered at the photoresist/ARC interface) with i-line photoresists such as OIR® 32 (OCG Corporation trademark) either when applied or baked.

Preferred polymer binders for ultra-thin ARCs incorporating the new dyes are copolymers with high glass transition temperatures such as polyamic acids, polyarylethers, polyarylsulfones, aromatic polyamides, solvent-soluble polyimides, and aromatic polyureas. Examples of especially useful binders include the following polymers:

1. polyamic acid prepared by the reaction of 4,4'-oxydianiline and pyromellitic dianhydride;

2. polyamide prepared from dimethyl terephthalate and 2,2,4-trimethylhexanediamine (known commercially as Trogamid®, Huls America trademark);

3. polysulfone prepared as the reaction product of 4,4,-isopropylidenediphenol and 4,4'-chlorophenylsulfone (known commercially as Udel®, Amoco Performance Products trademark);

4. polyurea prepared as the reaction product of bis(4-[4-aminophenyoxy]phenyl) sulfone and methylene-di-p-phenyl diisocyanate.

ARCs incorporating the new dyes are prepared by dissolving the polymer binder and the dye(s) in the preferred ARC solvents described above to a total solids concentration of 3 wt. % to 10 wt. %. The total solids concentration is adjusted so that when the coating is spin coated at 2000–6000 rpm for 30–90 seconds on a semiconductor substrate and then hot plate baked at 100°–220° C. for 30–120 seconds, the desired coating thickness will be obtained in the range of 0.05 microns to 0.25 microns. Spin coating at 2500–5000 rpm for 60–90 seconds is preferred to obtain defect-free coatings. Likewise, baking at 150°–210° C. for 30–60 seconds is preferred to achieve the best lithographic performance with most resists. (Defect-free refers to the absence of thickness variations, voids, pinholes, dewetted areas or particulate matter.) Organosilanes such as 3-aminopropyltriethoxysilane and/or surfactants such as Fluorad® FC-430 (3M Corporation trademark) may be added to the ultra-thin ARCS at levels of 0.01 wt. % to 0.5 wt. % to improve the adhesion and wetting characteristics of the coatings.

The following examples further illustrate the invention.

Example 1.

Preparation of bis-a-cyanoacrylamide dye from diamine, ethyl cyanoacetate, and vanillin

Procedure

To a 5 L, four-necked, round-bottomed flask equipped with a mechanical stirrer, thermometer, reflux condenser, and temperature probe with rheostat controller and heating mantle was added 197.56 g (1.70 mmol) of 2-methyl-1,5-pentanediamine. To this diamine was slowly added with stirring, 384.60 g (3.40 mmol) of ethyl cyanoacetate. The reaction of 2-methyl-1,5-pentanediamine and ethyl cyanoacetate produced an initial exotherm. When the exotherm subsided, the solution was heated at reflux for 1 h to give a clear, dark orange solution. Heating was temporarily removed and the solution diluted with 1200 ml of ethanol. To the diluted solution was added 517.32 g (3.40 mmol) of vanillin and 12.00 g (100.70 mmol) of N-methyldiethanolamine as a catalyst, followed by an additional 1200 ml of ethanol. Heating was re-applied and the dark orange solution maintained at reflux for 3.5 h. The solution was slightly cooled and 12.00 g (122.34 mmol) of concentrated sulfuric acid was added to neutralize the reaction mixture. The solution was stirred overnight at room temperature to allow the dye to crystallize from the solution.

The crystallized dye was collected by vacuum filtration using 500 ml of isopropanol for rinsing and washing. The collected dye was allowed to dry in the filtration funnel for 20 minutes and then washed twice with 1000 ml portions of deionized water to remove salts. Subsequently, it was washed with three 1000 mL portions of acetone to remove unreacted starting materials and soluble by products. The wet solid was placed in a glass baking dish and air dried for two days to give 620.20 g (70.6% yield) of light orange colored dye. The dye exhibited a molar extinction coefficient of 38,700 L/mol-cm in tetrahydrofurfuryl alcohol.

Example 2.

Preparation of bischalcone dye from hydroxyacetophenone and terephthaldehyde

Procedure

A 500 ml round-bottomed flask equipped with magnetic stirring bar and condenser was charged with 100 ml of ethanol, 12.40 g (74.6 mmol) of acetovanillone and 5.00 g (37.3 mmol) of terephthaldehyde. The stirred mixture was first warmed to give a solution and the solution then cooled to 15° C. To the stirred solution at 15° C. was added 66.0 g (181 mmol) of tetramethylammonium hydroxide (25 weight. % aqueous solution) over 18 min, with the temperature rising to a maximum of 25° C. The reaction flask was covered with aluminum foil to protect light sensitive chalcone and stirring continued at ambient for 2 days.

The resulting reaction product was added dropwise to 450 g of stirred 1.5N HCl. Solid terephthalaldehyde-derived chalcone was collected by filtration and washed on the filter with three 200 ml aliquots of deionized water, two 100 ml aliquots of ethanol, and two 25 ml portions of acetone. Drying gave 13.8 g (86% yield) of yellow bischalcone that exhibited a molar extinction coefficient in N-methypyrrolidone (NMP) of 42,112 L/mol-cm. About 13.4 g of the product was stirred with 150 ml of boiling ethanol for 0.5 h, the mixture filtered hot, the precipitate washed on the filter with 50 ml of acetone, and then dried to give 8.2 g (52% yield, overall). The melting point of the purified yellow diphenolic chalcone was 234°–239° C. and the extinction coefficient in NMP was 49,550 L/mol-cm.

Example 3.

Preparation of bischalcone dye from alkoxyacetophenone and terephthaldehyde

Procedure

A 250 ml round-bottomed flask equipped with magnetic stirring bar and condenser was charged with 82 ml of ethanol, 9.01 g (60.0 mmol) of 4-methoxyacetophenone, and 4.02 g (30.0 mmol) of terephthalaldehyde. The stirred mixture was heated gently to give a solution. To this stirred solution at 23° C. was added 28.1 g (77.0 mmol) of 25 weight % tetramethylammonium hydroxide over 16 min. During the hydroxide addition, a precipitate almost immediately formed. The base addition was interrupted, an additional 80 ml of ethanol added, the chalcone lump broken up, and the rest of the tetramethylammonium hydroxide added. The final reaction mixture temperature was 26° C. The reaction mixture was then protected with aluminum foil and stirred at ambient for 3 days. The mixture was placed in the freezer for several hours; and with the mixture temperature being 0° C., the product was collected by filtration. The bischalcone was washed on the filter with ethanol followed by three 300 ml portions of deionized water. After drying, the yield of crude cream-colored solid was 10.63 g (89%), mp 221°–246° C. The molar extinction coefficient in NMP was 44,700 L/mol-cm at 365 nm.

Examples 4–27.

The data for other representative dye structures from Families 1–3 are summarized in Table I.

See Table I, Dye Examples 4–27

Example 28.

Using a dichalcone dye in a polyamic acid-based ARC

The dichalcone dye described in Example 2 was dissolved in a polyamic acid solution formulated with solvents NMP and cyclohexanone to achieve a weight ratio of dye to other ingredients (excluding solvents) of 0.67:1.00. This ARC formulation was spincoated onto three separate glass slides at 5000 rpm for 60 seconds. The three slides were baked on a hot plate at respective temperatures of 168°, 200°, and 230° C. for 60 seconds. For adjusted film thicknesses of 1300 Å, the absorbances at I-line were 0.61, 0.60, and 0.59, indicating that dye sublimation was not occurring as bake temperature increased.

To demonstrate the lithographic capability of the ARC, the formulation was spin coated at 5000 rpm for 60 seconds onto a silicon wafer that had been treated with Brewer Science's APX adhesion promoter and the coating was then baked on a hot plate at 168° C. for 60 seconds. A positive-working photoresist (Shipley Microposit® 1470) soluble in propylene glycol methyl ether acetate (PGMEA) was immediately applied over the ARC by spin coating at 5000 rpm for 30 seconds. The resist was soft baked for 30 seconds for 60 seconds at 200° C. to obtain a defect-free film with a thickness of 1332 Å (by ellipsometry). An ethyl lactate-based, i-line photoresist capable of submicron resolution (IX 500 EL from Japan Synthetic Rubber) was spin coated over the ARC and soft baked at 100° C. for 90 seconds in proximity. The resist was exposed with a Nikon I-line stepper (0.50 numerical aperature) for 580 msec and then

TABLE I

DYE EXAMPLES 4–27

| FAMILIES 1 & 2 Example | Aldehyde | Spacer Group | Family | Formula Weight (g/mole) | Extinction Coefficient (L/mole-cm × 10⁻⁴) |
|---|---|---|---|---|---|
| 4 | cinnamaldehyde | 4,4'-diacetylphenyl ether | 1 | 482 | 5.69 |
| 5 | N,N-dimethylamino-benzaldehyde | 2-methyl-1,5-pentanediamine/ECA* | 2 | 513 | 3.65 |
| 6 | furylcrolein | 1,3-propanediamine/ECA | 2 | 416 | 5.83 |
| 7 | hydroxybenzaldehyde | 2-methyl-1,5-pentanediamine/ECA | 2 | 459 | 2.18 |
| 8 | 3,4-dimethoxybenzaldehyde | 2,2,4-trimethylhexanediamine/ECA | 2 | 589 | 4.73 |
| 9 | 3,4-dimethoxybenzaldehyde | amine-terminated urethane oligomer/ECA | 2 | 802 | 4.79 |
| 10 | cinnamaldehyde | di(2-hydroxyethyl) ester of PMDA**/ECA | 2 | 707 | 5.55 |
| 11 | vanillin | 1,2-propanediamine/ECA | 2 | 477 | 3.81 |
| 12 | 3,4-dimethoxybenzaldehyde | 2-methyl-1,5-pentanediamine/ECA | 2 | 547 | 4.68 |

| FAMILY 3 | Reactant with Terephthaldicarboxaldehyde | Yield (%) | MP (°C.) | | |
|---|---|---|---|---|---|
| 13 | 4-hydroxyacetophenone | 82 | — | 370 | 3.32 |
| 14 | acetophenone | — | — | 338 | 3.83 |
| 15 | N-2-hydroxyethyl cyanoacetamide | 77 | 237 | 354 | 2.65 |
| 16 | 4-hydroxy-2-methylacetophenone | 60 | 250–255 | 398 | 3.18 |
| 17 | 4-hydroxy-3-methylacetophenone | — | — | 398 | 4.80 |
| 18 | 3,4-dimethoxyacetophenone | 80 | 200–216 | 458 | 5.34 |
| 19 | 2-hydroxy-6-methoxyacetophenone | 70 | 199–205 | 430 | 4.09 |
| 20 | 4-hydroxy-3,5-dimethoxyacetophenone | 54 | 245–250 | 490 | 4.27 |
| 21 | 2-hydroxy-4-methoxyacetophenone | 46 | 230–243 | 430 | 3.49 |
| 22 | 2-hydroxy-5-methoxyacetophenone | 58 | 152–210 | 430 | 1.68 |
| 23 | 2-hydroxyacetophenone | 65 | 223–245 | 370 | 1.99 |
| 24 | 3-hydroxyacetophenone | 98 | 210–213 | 370 | 1.41 |
| 25 | 2,4-dihydroxyacetophenone | 88 | — | 402 | 1.39 |
| 26 | 4-hydroxy-2-methylacetophenone | 60 | 250–255 | 398 | 3.18 |
| 27 | 4-hydroxyethoxyacetophenone | 85 | 249–255 | 458 | 3.71 |

[*/ECA denotes reaction product of diamine with two moles of ethyl cyanoacetate; **PMDA is pyromellitic dianhydride.]

on a hot plate at 100° C. and exposed on a stepper with a mercury-xenon light source. The specimen was then developed in aqueous tetramethylammonium hydroxide (Shipley MF®-319 developer) for 45 seconds at ambient temperature to clear the exposed areas of the resist and those portions of the ARC immediately beneath the exposed resist. Microscopic examination showed that the cleared areas were residue-free and that stable 0.7 μm features were resolved.

Example 29.

Using a bis-a-cyanoacrylamide dye in a polyurea-based ARC

An ARC formulation was prepared by combining 144.40 g of 20% solids polyurea solution in tetrahydrofurfuryl alcohol (THFA), 23.10 g of the bis-a-cyanoacrylamide dye from Example 1, 568.58 g of cyclohexanone, and 379.06 g of THFA. (The polysulfone was a copolymer of bis(4-[4-aminophenoxy]phenyl)sulfone and methylene-di-p-phenyl diisocyanate.) The solution was ion exchanged with 50 g of Rohm and Haas Amberlite® 200C(H) ion exchange beads for 4 h to remove ionic contaminants. A sample was then taken and the thickness checked to give 1300 Å±50 Å. The ion exchange beads were removed with a coarse screen and the final formulation filtered through a 0.2 μm capsule filter.

Figure 1:
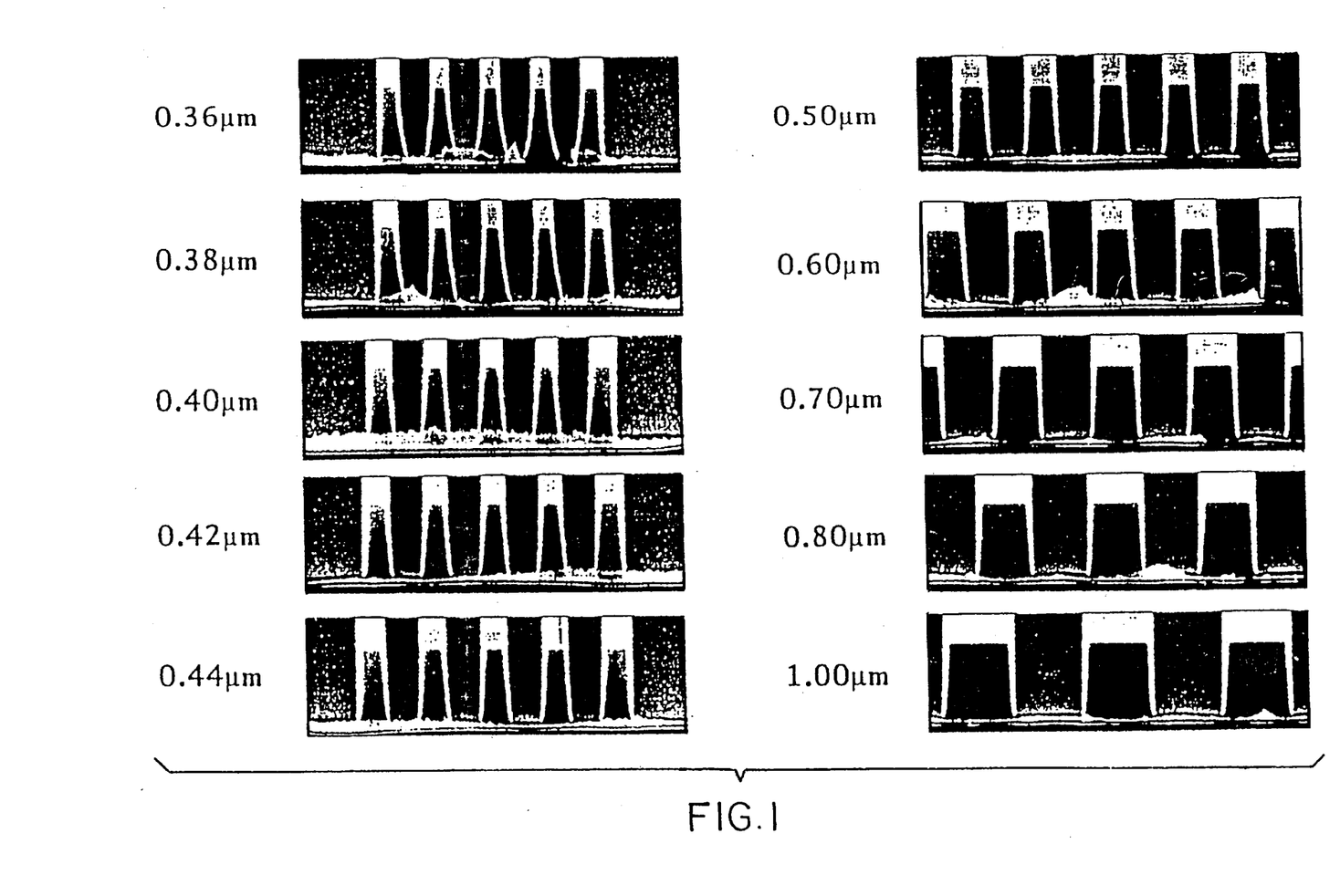
FIG. 1 depicts line and space patterns from micrographs described in Example 29.
Figure 2:
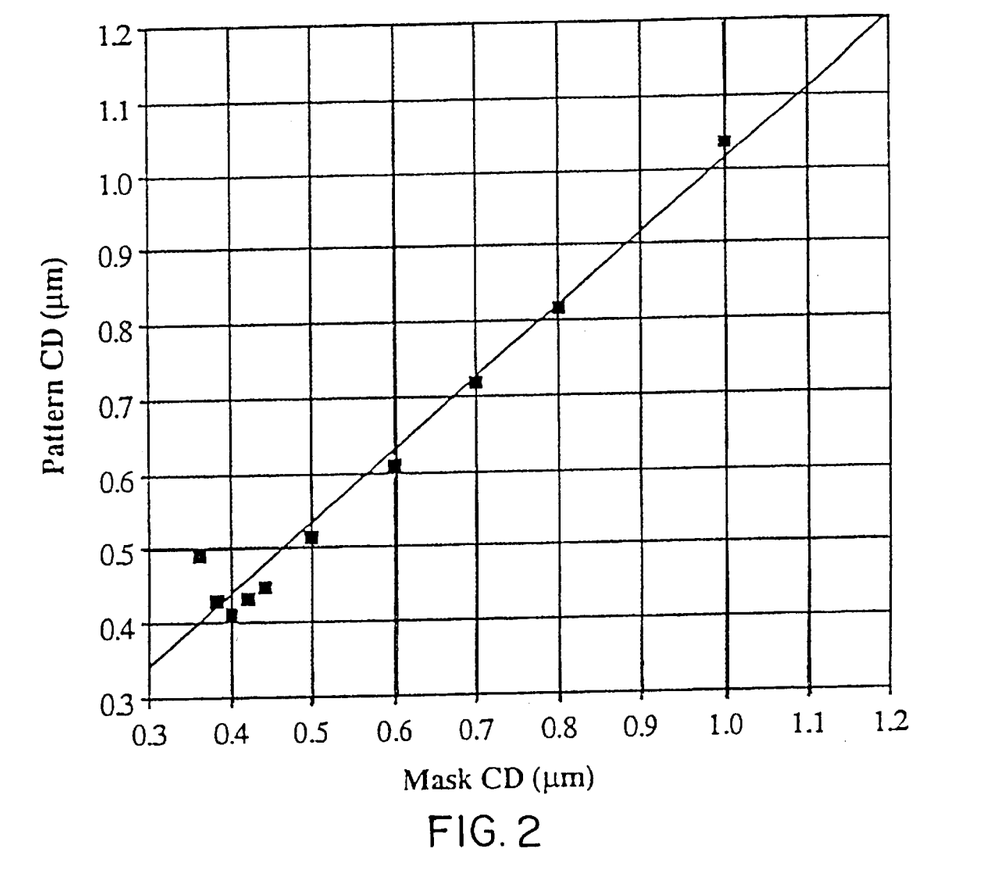
FIG. 2 depicts the linearity of the pattern critical dimension (CD) and mask (CD) of Example 29.

The experimental ARC was spin coated for 60 seconds at 2500 rpm onto a 6", silicon wafer and baked on a hot plate post-exposure baked at 110° C. for 90 seconds in proximity. The wafer specimen was then single-puddle developed for 40 seconds in aqueous tetramethylammonium hydroxide to generate the line & space patterns shown in FIG. 1. "The SEM pictures illustrated in FIG. 1 are pictures of the linearity of SEM Pictures for the Linearity of Exp93040/ IX500EL on NSR 1755i7A (0.50NA) Stepper Exp93040: 2500RPM, 200° C. Bake, Thk=1332A IX500EL: Thickness=1.07 μm 40" Single Puddle Develop, Exp=580 msec" (The unetched ARC film can be seen beneath and between the resist features.) The high quality of the resist features, i.e., the presence of highly vertical resist feature sidewalls and the absence of any rounding at the bottom of the resist features, as well as the linearity of the pattern critical dimension (CD) and mask CD (FIG. 2) was evidence of the excellent compatibility of the ARC and photoresist.

Example 30.

Using a sublimable, photoresist-soluble dye in a polyimide-based ARC. Comparison with performance of ARC from Example 28.

Dicinnamalacetone (DCA, structure shown below) was selected as an example of a highly absorbing I-line dye which is sublimable at ARC processing temperatures and is soluble in photoresist solvents such as propylene glycol methyl ether acetate (PGMEA). ARCs were prepared from DCA and evaluated to demonstrate 1) the negative relationship between bake temperature and film absorbance and 2) the excessive removal of DCA from the film during photoresist application.

Dicinnamalacetone

Formula Weight=286.38 g/mol
MP=145° C.

Dicinnamalacetone was combined with polyamic acid solution (in NMP and cyclohexanone) in a manner similar to that described in Example 28 to form ARCs with weight ratios of DCA to other ingredients of 0.60:1.00 and 0.80:1.00. (These values correspond to coated films which contain 37.5 wt. % and 44.4 wt. % dye, assuming the proportions of the ingredients remain the same during the spin coating process.) The two ARCs were spin coated onto round glass slides at 4000 rpm (60 sec) and baked on a hot plate at these respective temperatures: 150°, 168°, 190°, and 210° C. The film thickness (by profilometry) and film absorbance of each specimen were measured shortly after baking. Subsequently, the specimens were placed back on the spin coater and liquid PGMEA was puddled on the coating for five seconds in a static condition and then spun until dry. Film absorbance was then redetermined. (The absorbance loss of the ARC resulting from PGMEA application can be correlated with absorbance loss during the application of a photoresist, a process commonly known as stripping.) The initial film thickness and absorbance data before and after PGMEA application are presented in Table II.

TABLE II

Film Thickness and Film Absorbance for Dicinnamalacetone-Loaded Polyamic Acid-Based ARC as a Function of Bake Temperature and Before and After PGMEA Application

| Calculated Wt. % DCA in ARC film | Bake Temperature (°C.) | Film Thickness (Å) | Film Absorbance at 365 nm | | |
|---|---|---|---|---|---|
| | | | Before | After | % Loss |
| 37.5 | 150 | 1327 | 0.7543 | 0.4885 | 35.2 |
| 37.5 | 168 | 1215 | 0.6361 | 0.4840 | 23.9 |
| 37.5 | 190 | 1013 | 0.4299 | 0.4285 | 0.3 |
| 37.5 | 210 | 902 | 0.2027 | 0.2026 | 0.0 |
| 44.4 | 150 | 1522 | 0.9741 | 0.4265 | 56.2 |
| 44.4 | 168 | 1416 | 0.8331 | 0.5239 | 37.1 |
| 44.4 | 190 | 1058 | 0.5494 | 0.5209 | 5.2 |
| 44.4 | 210 | 915 | 0.2095 | 0.1976 | 5.7 |
| Example 28 ARC containing using 40.1 wt. % Family 3 dye | 168 | 1565 | 0.7206 | 0.6845 | 5.0 |
| | 200 | 1545 | 0.7171 | — | — |
| | 230 | 1495 | 0.6799 | — | — |

The results showed that DCA-loaded ARCs, though highly absorbant at i-line, showed significant sublimative losses as bake temperature increased from 150° C. to 210° C. This was evidenced by a sharp monotonic decrease in starting film absorbance and film thickness as bake temperature was raised. The films were also highly susceptible to stripping by PGMEA (as measured by % Loss), particularly at the lower bake temperatures. As expected, stripping was more severe for the ARC prepared with a higher dye loading. These results could be contrasted with those (bottom of Table II) for the Example 28 ARC which showed virtually no stripping or sublimative loss at a comparable dye loading.

Example 31.

Using a sublimable, photoresist-soluble dye in a polyurea-based ARC. Comparison with performance of ARC from Example 29.

An ARC similar to the polyurea composition described in Example 29 was prepared by combining DCA with polyurea in a mixture of THFA and cyclohexanone. The ARC was formulated to provide 28.6 wt. % DCA in the coated film. It was spin coated onto round glass slides at 5500 rpm (60 sec) which were baked on a hot plate at these respective temperatures: 168°, 190°, and 220° C. The film thickness (by profilometry) and film absorbance of each specimen were measured shortly after baking. A PGMEA-based resist (Shipley Microposit® 1470) was spin coated over the ARC and then immediately removed by spraying the specimen with PGMEA for five seconds while spinning. Film absorbance was remeasured to determine the degree of dye stripping resulting from the resist apply and removal process. The initial film thickness and absorbance data before and after resist application are presented in Table III.

TABLE III

Film Thickness and Film Absorbance for a Dicinnamalacetone-Loaded Polyurea-Based ARC as a Function of Bake Temperature and Before Resist Application and After Resist Removal

| Calculated Wt. % DCA in ARC film | Bake Temperature (°C.) | Film Thickness (Å) | Film Absorbance at 365 nm | | |
|---|---|---|---|---|---|
| | | | Before | After | % Loss |
| 28.6 | 168 | 2180 | 0.6571 | 0.2614 | 60.2 |
| 28.6 | 190 | 1980 | 0.3483 | 0.1708 | 51.0 |
| 28.6 | 220 | 1800 | 0.1275 | 0.0904 | 29.1 |
| Example 37 ARC containing 44.4 wt. % Family 1 dye | 200 | 1485 | 0.5498 | 0.4259 | 22.5 |
| | 220 | 1460 | 0.5371 | 0.4292 | 20.1 |

As in Example 30, the DCA-loaded films showed a sharp drop in absorbance and thickness as bake temperature increased, indicating that dye sublimation was occurring. Likewise, resist application and removal caused a significant reduction in ARC absorbance at all bake temperatures because of the high solubility of DCA in the resist solvent, PGMEA. It should be noted that stripping levels were high even though the DCA content in the as-spun films was low. The Example 29 ARC (see bottom of Table III), on the other hand, exhibited much less stripping than the DCA-loaded ARC at a higher dye loading. The film thickness and absorbance of the Example 29 ARC were also stable at the bake temperatures used in the study.

What is claimed is:

1. The mid-UV-absorbing bis-α-cyano-acrylamide dyes represented by the structural formula:

where $R_1$ is chosen from the group consisting of:

where $R_3$ is hydrogen, methyl, halogen, hydroxyl, or methoxyl; and $R_2$ is a divalent organic radical selected from the group consisting of:

$-CH_2-CH_2-$   $-CH_2-CH_2-CH_2-$ $-(CH_2)_6-$   and   $-CH_2-CH_2-O-CH_2-CH_2-$.

2. The dye of claim 1 corresponding to the following structural formula: